United States Patent
Weinschenk, III et al.

(10) Patent No.: US 6,599,317 B1
(45) Date of Patent: Jul. 29, 2003

(54) INTRAOCULAR LENS WITH A TRANSLATIONAL ZONE

(75) Inventors: Joseph I. Weinschenk, III, Ft. Worth, TX (US); Charles X. Liao, Irvine, CA (US); Massoud Ghazizadeh, Laguna Nigel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 47 days.

(21) Appl. No.: 09/657,251

(22) Filed: Sep. 7, 2000

(65) Prior Publication Data (65)

Related U.S. Application Data
(60) Provisional application No. 60/154,745, filed on Sep. 17, 1999.

(51) Int. Cl.[7] .................................................. A61F 2/16
(52) U.S. Cl. ...................... 623/6.34; 623/6.37; 623/6.28
(58) Field of Search ............................. 673/6.11, 6.13, 673/6.22, 6.24, 6.27–6.39, 6.43–6.44, FOR 105

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | Feinbloom |
| 3,339,997 A | 9/1967 | Wesley |

(List continued on next page.)

FOREIGN PATENT DOCUMENTS

| | | |
|---|---|---|
| AU | 3225789 | 10/1989 |
| DE | 2702117 | 7/1978 |
| DE | 3246306 | 6/1984 |
| EP | 0246216 | 11/1987 |
| EP | 0329981 | 8/1989 |
| EP | 0337390 | 10/1989 |
| EP | 0342895 | 11/1989 |
| EP | 0351471 | 1/1990 |
| EP | 0566170 | 10/1993 |
| EP | 0691109 | 1/1996 |
| EP | 0897702 | 2/1999 |

(List continued on next page.)

OTHER PUBLICATIONS

Menzo et al. J Cataract Refract. Surg 24, Aug. 1998, pp. 1039–1049.
Fechner et al. J Cataract Refract. Surg 24, Jan. 1998, pp. 48–56.
Amo Specs, Model AC–218, 1992, 5 pages.
Chiron Vison, Nutiva MA20, 1997, 6 pages.
Thornton, Accommodation in Pseudophakia, 25, pgs. 159–162.
Video Tape "New Elliptical Acco. IOL for Cataract Surgery," shown at ASCRS Symposium on Apr. 10, 1999.

*Primary Examiner*—David H. Willse
(74) *Attorney, Agent, or Firm*—Stout, Uxa, Buyan & Mullins LLP; Frank Uxa; Peter Jon Gluck

(57) ABSTRACT

An intraocular lens (IOL) for use in a mammalian eye includes an optic adapted to focus light toward a retina of the mammalian eye and, in cooperation with the mammalian eye, to provide accommodation, the optic including a first portion adapted to move in response to the action of the mammalian eye; and a second portion secured to the first portion and having a higher index of refraction than the first portion and/or being positioned generally anterior of the first portion.

31 Claims, 2 Drawing Sheets

U.S. PATENT DOCUMENTS

| | | |
|---|---|---|
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsuetaki et al. |
| RE32,525 E | 10/1987 | Pannu |
| 4,702,244 A | 10/1987 | Mazzocco |
| 4,704,016 A | 11/1987 | De Carle |
| 4,720,286 A | 1/1988 | Bailey et al. |
| 4,725,278 A | 2/1988 | Shearing |
| 4,731,078 A * | 3/1988 | Stoy et al. .................. 623/6.13 |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell, Delmar R. et al. |
| 4,938,583 A | 7/1990 | Miller |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider et al. |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,549,760 A | 8/1996 | Becker |
| 5,562,731 A | 10/1996 | Cumming |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,814,103 A | 9/1998 | Lipshitz et al. |
| 5,843,188 A | 12/1998 | McDonald |
| 5,876,442 A | 3/1999 | Lipshitz et al. |
| 6,013,101 A | 1/2000 | Israel |
| 6,096,078 A | 8/2000 | McDonald |
| 6,176,878 B1 | 1/2001 | Gwon et al. |
| 6,217,612 B1 | 4/2001 | Woods |

FOREIGN PATENT DOCUMENTS

| | | |
|---|---|---|
| GB | 2124500 | 2/1984 |
| GB | 2129155 | 5/1984 |
| GB | 2192291 | 1/1988 |
| GB | 2215076 | 9/1989 |
| WO | 2058391 | 4/1981 |
| WO | 2146791 | 4/1985 |
| WO | 8603961 | 7/1986 |
| WO | 8700299 | 1/1987 |
| WO | 8707496 | 12/1987 |
| WO | 8902251 | 3/1989 |

| | | | | | |
|---|---|---|---|---|---|
| WO | 8911672 | 11/1989 | WO | 9625126 | 8/1996 |
| WO | 9416648 | 8/1994 | WO | 9743984 | 1/1997 |
| WO | 9503783 | 2/1995 | WO | 0134067 | 5/2001 |
| WO | 9615734 | 5/1996 | | | |

* cited by examiner

INTRAOCULAR LENS WITH A TRANSLATIONAL ZONE

RELATED APPLICATION

This application claims the benefit of provisional application Ser. No. 60/154,743 filed Sep. 17, 1999 and entitled INTRAOCULAR LENS WITH A TRANSLATIONAL ZONE.

BACKGROUND OF THE INVENTION

The present invention relates to intraocular lenses (IOLs). More particularly, the invention relates to IOLs with one or more translational zones which are adapted to provide accommodation in the eye.

The human eye includes an anterior chamber between the cornea and iris, a posterior chamber, defined by a capsular bag, containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near and distant vision, respectively. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently, multifocal IOLs without accommodating movement have been used to provide near/far vision correction.

Attempts have been made to provide IOLs with accommodating movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. The disclosure of each of these patents is incorporated herein by reference. One problem that exists with such IOLs is that they often cannot move sufficiently to obtain the desired accommodation.

It would be advantageous to provide IOLs adapted for accommodating movement which can achieve an increased amount of accommodation.

SUMMARY OF THE INVENTION

New accommodating IOLs have been discovered. The present accommodating IOLs take advantage of employing an optic made of two different materials to enhance the accommodation achievable in the eye in response to normal accommodative stimuli. Thus, the present lenses provide for controlled vision correction or focusing for both near objects and far or distant objects. Further, a greater overall range of accommodation is often achieved. The present IOLs are relatively straightforward in construction and to manufacture or produce, can be implanted or inserted into the eye using systems and procedures which are well known in the art and function effectively with little or no additional treatments or medications being required.

In one broad aspect of the present invention, intraocular lenses (IOLs) are provided and comprise an optic adapted to focus light toward a retina of a mammalian eye and, in cooperation with the mammalian eye, to provide accommodation. The optic includes a first lens portion adapted to move in response to the action of the mammalian eye; and a second lens portion secured to the first portion of the optic and having a higher refractive index than the first portion and/or being positioned generally anterior of the first portion. The first lens portion is comprised of an optically clear material that is easily reshaped and/or is axially movable when exposed to force exerted by the mammalian eye.

In one embodiment, the second lens portion of the optic is comprised of an optically clear material having a higher refractive index than the first lens portion. For example, the first portion may have a refractive index of about 1.37 or less, while the second portion preferably has a refractive index of at least about 1.42. The difference in refractive index between the first and second portions preferably is in the range of at least 0.03 and more preferably is in the range of about 0.04 to about 0.1 or more. The second portion of the optic preferably is positioned generally anterior of the first portion. More preferably, the second portion includes an anterior surface which defines at least a portion of the anterior face of the optic.

The second lens portion may be reshapable by the force exerted on the optic by the eye or may be substantially rigid in response to such force. As a result of this, potential materials of construction for the second portion may vary significantly.

The present lenses very effectively provide for both enhanced movement, for example, reshaping and/or axial movement, because of the substantially compliant or deformable first lens portion, while, at the same time, providing for relatively high refractive index and therefore effective corrective optical powers with a reduced sized lens because of the higher refractive index second lens portion. This combination of enhanced movement and high refractive index provides a substantial benefit in achieving accommodation in the mammalian eye.

In one very useful embodiment, the first lens portion of the optic is adapted to be reshaped in response to the action of the mammalian eye. Alternately, or in conjunction with the reshaping of the first portion, this first portion may be adapted to move axially in the mammalian eye in response to the action of the mammalian eye.

To achieve further enhanced accommodation, the optic preferably further comprises a third lens portion spaced apart from the second lens portion, secured to the first lens portion, and having a higher refractive index than the first portion, more preferably substantially the same refractive index as the second portion, and/or positioned generally posterior of the first portion. Advantageously, the second and third portions are located so that their central axes are aligned with the optical axis of the optic. Looked at from another perspective, the second portion may be considered as an anterior lens portion while the third portion may be considered a posterior lens portion. The first portion preferably is situated between the second and third portions.

The embodiment of the present IOLs with the optic including second and spaced apart third lens portions is advantageous in that the optic is still responsive to the force exerted by the eye on the optic while, at the same time, the positioning and/or refractive indexes and/or optical powers of the second and third portions provide for obtaining enhanced accommodation with such an optic. The second lens portion, for example, the anterior lens portion, may have a higher, preferably positive, optical power than the third lens portion, for example, the posterior lens portion. In other words, the second lens portion can have a positive optical power relative to the baseline optical power, which is the optical power for distance vision correction, and the third lens portion can have a negative optical power relative to the baseline optical power. The use of lens portions with positive and negative optical powers, for example, highly positive and highly negative optical powers, extends the total accommodative dioptic change beyond that of the movement of a single lens design. Such positive/negative lens portions including a relatively easily deformable first portion provide a larger dioptic power change relative to a single lens design based on the same amount of movement of the lens in the eye. Thus, increased or enhanced amounts of accommodation are provided using the present optics including positive and negative lens portions.

As noted previously, the second and third lens portions of the optic may have substantially the same refractive index. More preferably, the second and third portions of the optic are made of substantially the same material, that is material having substantially the same chemical makeup. The refractive index of each of the second portion and the third portion of the optic preferably is at least about 1.42.

The reshaping or deformation of the first lens portion can cause an axial movement of the first portion which imparts an axial movement of the second lens portion, or the second and/or third portions of the optic. Axial movement of the second portion or the second and/or third portions of the optic have a relatively large effect on the accommodative power of the optic. Thus, providing axial movement of the second portion, or the second and/or third portions of the optic is one important feature of the present invention. Of course, reshaping of the first portion in and of itself may provide accommodative power. The overall accommodative power of the optic in accordance with the present invention preferably is increased beyond the accommodation obtained by the axial movement of a single lens of uniform composition, for example, because of the reshaping or deformation of the first portion and/or the presence of the third portion.

In another very useful embodiment, a force transfer assembly is provided. This force transfer assembly has a first end coupled to the optic and a second end extending away from the optic and adapted to contact a posterior bag of the mammalian eye when the IOL is located in the mammalian eye. The force transfer assembly is adapted to transfer the force exerted by the eye to the optic to facilitate the movement of the optic. Preferably, the force transfer assembly is adapted to transfer the force exerted by the eye to the optic to facilitate at least one of reshaping the first portion in response to the action of the mammalian eye and moving the first portion axially in the mammalian eye in response to the action of the mammalian eye. In a very useful embodiment, the force transfer assembly is adapted to transfer force from the eye to the optic to both facilitate reshaping of the optic and moving the optic, for example, at least a portion of the optic, axially in the eye. The force transfer assembly is very effective in facilitating the accommodation obtained by the present IOLs.

However, it should be noted that such force transfer assembly is not essential in accordance with the present invention. The optic can be sized and configured to fit within the capsular bag and to contact the capsular bag, in particular the periphery of the capsular bag, so that the force exerted by the eye can be transferred directly to the optic of the present IOL. Such IOLs in which the optics are sized and configured to contact the peripheral capsular bag are very effective in being reshaped to provide the desired accommodation. In addition, substantially filling the capsular bag volume with a deformable optic including a first portion and a second portion and possibly a third portion as in the present optics, reduces the risk of decentration or tilt of the lens system in the eye, as well as reducing the risk of decentration or tilt between individual lens components, relative to lens systems in which the optic does not substantially fill the capsular bag volume. Providing for a reduced risk of decentration is highly advantageous, for example, as the capsular bag contracts. Even if the contraction of the capsular bag is asymmetric, for example, because the zonules are not of uniform strength, the elastic properties of the first portion mitigate against this asymmetry and reduce the risk of decentration.

Substantially filling the capsular bag volume, as described above, may reduce the risk of posterior capsular opacification (PCO) particularly if the posterior surface or face of the optic remains in contact with the posterior wall of the capsular bag during all states of accommodation.

In a very useful embodiment, the present IOLs are deformable for insertion into the mammalian eye through a relatively small incision, for example on the order of about 3.5 mm or less. Thus, both the first and second portions of the optic, and the third portion of the optics and/or the force transfer assembly, if present, are all deformable for insertion through a small incision into the eye. Such IOLs regain their original undeformed condition rapidly after being inserted into the mammalian eye.

In order to facilitate the movement in the eye, the first portion preferably is more deformable than the second portion and the third portion, if present, of the present IOLs. As noted previously, the second portion, and the third portion, if present, can be substantially rigid, for example, in response to forces exerted by the eye. However, it is preferred that the entire IOL be sufficiently deformable to be passed through an incision in the eye which is less than the diameter of the IOL in its undeformed condition.

The present optics may be made of any suitable materials of construction. For example, the present optics may be made of one or more polymeric materials employing techniques used in manufacturing conventional polymeric material IOLs. Examples of the materials from which the present optics can be made include, without limitation, acrylic polymeric materials, silicone polymeric materials, and the like and combinations thereof. Although combinations of different polymeric materials may be employed, the present optics preferably are made of different polymeric materials of the same general chemical family. For example, the first portion of the IOL may be made of one silicone polymeric material while the second portion and third portion, if present, are made of a different silicone polymeric material. Similarly, the first portion of the optic can be made of one acrylic polymeric material while the second portion and third portion, if present, are made of a different acrylic polymeric material. In any event, the first portion of the present optics and the second portion and third portion, if present, preferably are made of compatible materials of construction, that is materials which can be used to produce an effective IOL which remains as an intact structure in the eye without significant deterioration for periods of time extending for at least about 20 or about 25 years or more.

In one embodiment, the first lens portion of the present optics is made of a very low modulus silicone polymeric material, while the second lens portion and third lens portion, if present, are made of a higher refractive index silicone. To illustrate, the first portion of the optic can be composed of a silicone polymeric elastomer with the following material properties:

Optically clear;

Refractive index of at least about 1.37;

Shore A hardness of about 0; and

At least about 1000% elastic elongation.

The second lens portion, and third lens portion, if present, of the present optics can be made of a different silicone elastomer with the following material properties:

Optically clear;

Refractive index of about 1.42 or higher;

Shore A hardness in a range of about 0 to about 30; and

An elastic elongation higher than about 150%, preferably in a range of about 150% to about 400%.

The second lens portion and third lens portion, if present, can be made of widely varying materials. Examples include, without limitation, rigid and foldable acrylic polymeric materials, rigid and foldable non-acrylic polymeric materials, deformable or foldable silicone polymeric materials and the like and combinations thereof. The second portion and third portion, if present, can be hydrophobic or hydrophilic.

Many materials which meet the above-noted criteria are conventional and well known in the art. Therefore, a detailed description of such compositions is not presented here.

However, by way of illustration, the following materials of construction, based on constituent monomeric components, is presented.

TABLE

POTENTIAL FORMULATIONS

| Component | First Portion | Second Portion |
|---|---|---|
| 2-phenylpropyl acrylate | 50% wt. | 70% wt. |
| 2-phenylpropyl methacrylate | | |
| Ethylene glycol dimethacrylate | 0.5% wt. | 1.0% wt. |
| N-hexyl acrylate | 48.9% wt. | 28.4% wt. |
| UV chromophore (benzotriazole-type) | 0.5% wt. | 0.5% wt. |
| Initiator | 0.1% wt. | 0.1% wt. |

The present optics are conveniently produced using conventional and well known techniques, such as molding techniques. In one embodiment, the second portion, and third portion, if present, are produced in a separate mold and then inserted into a mold into which is placed the monomeric or partially polymerized monomeric mixture of the first portion precursors. The combination is then heated to elevated temperatures, for example on the order of about 40° C. to about 100° C., and/or subjected to ultraviolet radiation and the composition combination is allowed to cure, preferably for about one hour to about 24 hours. The material in the mold is then post-cured, preferably at a temperature in the range of about 70° C. to about 130° C., and/or by being subjected to ultraviolet radiation for a period of time, preferably for about two hours to about 30 hours. After curing (and post-curing), the mold is disassembled and the molded lens body recovered.

The force transfer assembly, if present, can be made or provided separately and then coupled to the optic or lens body, for example, in a mold in which the optic is cured or post-cured. Alternately, the force transfer assembly can be coupled to the lens body after the lens body is formed. Conventional techniques can be employed. For example, one or more recesses can be formed in the optic and the force transfer assembly can be secured to the optic by having an end placed in the recess, for example, in much the same manner in which a haptic or fixation member is secured to the optic of a conventional IOL.

Any suitable material or combination of materials of construction may be utilized in the force transfer assembly and the force transfer assembly can have any suitable configuration provided that such assembly is effective to at least partially transfer the force of the eye to the optic of the IOL. The force transfer assembly preferably is more rigid or less flexible than the first portion of the optic. However, the force transfer assembly preferably is sufficiently deformable to be folded or otherwise deformed to pass through a small incision for insertion into the eye. The force transfer assembly can be a single member substantially surrounding the optic, or can be a plurality, for example, about 2 or about 3 to about 4 or about 6, individual elements positioned around the peripheral edge of the optic. Although the force transfer assembly can include at least one hinge to facilitate axial movement of the optic in response to the action of the eye, preferably the force transfer assembly does not include a hinge.

The force transfer assembly preferably is made of a material or materials which are compatible with the eye and with the other material or materials included in the IOL. Examples of materials which can be included in the present force transfer assemblies include, but are not limited to, polypropylene, silicone polymeric materials, acrylic polymeric materials including but not limited to polymethylmethacrylate (PMMA), polyamides and the like and combinations thereof.

In a further broad aspect of the present invention, methods for inserting an IOL in an eye are provided. Such methods comprise providing an IOL in accordance with the present invention, as described herein. The IOL is placed into the eye, for example in the capsular bag of the eye, using equipment and techniques which are conventional and well known in the art. The IOL is placed in the eye so that the eye effectively cooperates with the IOL to provide accommodation as desired. After the IOL is inserted into the eye, any incision in the eye is closed. After a relatively short period of recuperation, the IOL provides the wearer of the IOL with substantially effective accommodation. No further treatments or medications, for example, to paralyze the ciliary muscle, to facilitate fibrosis or otherwise influence the position of the IOL in the eye, are required. Preferably the optic is deformed prior to being placed into the eye. Once the IOL is placed in the eye, and after a normal period of recovery from the surgical procedure, the IOL, in cooperation with the eye, provides the mammal or human wearing the IOL with the desired accommodation.

Any and all features described herein and combinations of such features are included within the scope of the present invention provided that the features of any such combinations are not mutually inconsistent.

Additional aspects and advantages of the present invention are set forth in the following description and claims, particularly when considered in conjunction with the accompanying drawings in which like parts bear like reference numerals.

DETAILED DESCRIPTION OF THE DRAWINGS

Figure 1:
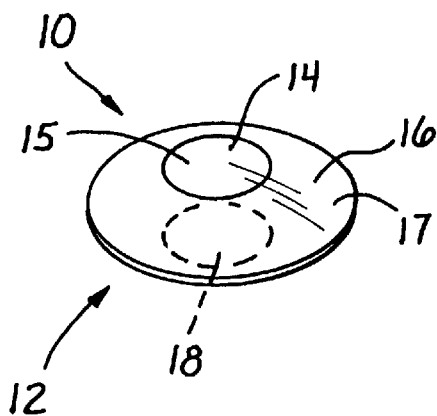
FIG. 1 is a top side view, in perspective, of an IOL in accordance with the present invention.
Figure 2:
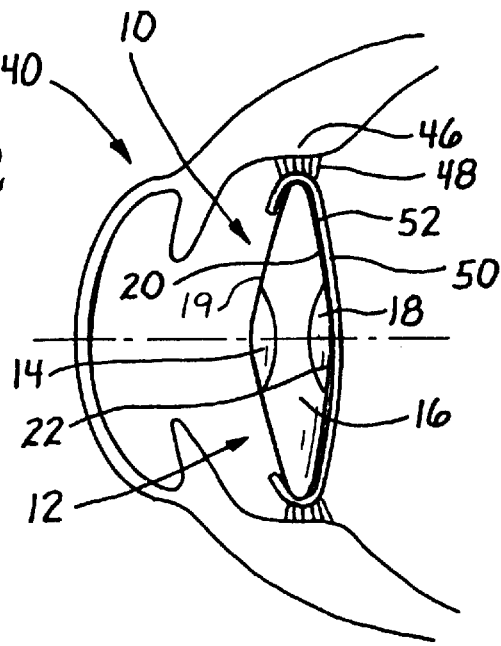
FIG. 2 is a fragmentary sectional view of an eye in which the IOL of FIG. 1 has been implanted, with the lens being located in a resting position with the ciliary muscle of the eye in the relaxed state.
Figure 3:
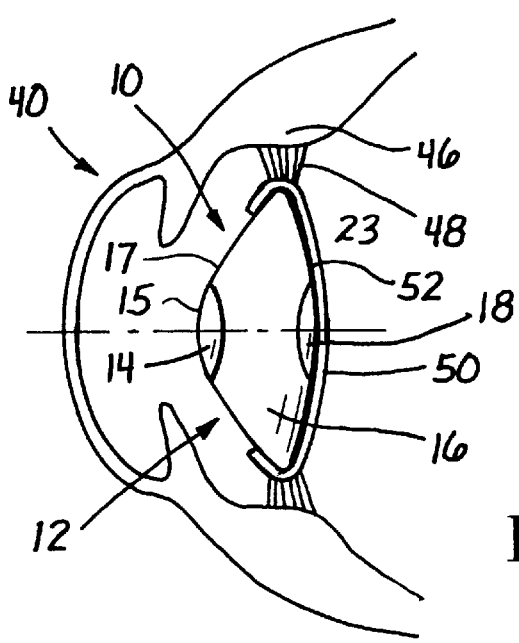
FIG. 3 is a fragmentary sectional view of an eye in which the IOL of FIG. 1 has been implanted, with the ciliary muscle of the eye in the contracted state.

Referring now to FIGS. 1, 2 and 3, an IOL according to the present invention, shown generally at 10, includes a lens body or optic 12. This optic 12 includes a combination of components, that is, anterior lens portion 14, central portion 16, and posterior portion 18.

The anterior lens portion 14 and posterior lens portion 18 are made of an optically clear material with a refractive index of at least about 1.42, for example, about 1.48. Each of these lens portions 14 and 18 are made of a material having substantially the same chemical makeup, although this is not essential. Further, the lens portions 14 and 18 can be either deformable or rigid. Preferably the lens portions 14 and 18 are sufficiently deformable so as to be foldable or otherwise deformed for insertion into the eye through a small incision, that is an incision in the eye smaller than the maximum, undeformed diameter of the optic 12. However, the anterior and posterior lens portions 14 and 18 preferably are more rigid than is the central lens portion 16.

The anterior lens portion 14 includes an anterior surface 15, the central lens portion 16 includes an anterior surface 17 and a posterior surface 20, and the posterior lens portion 18 includes a posterior surface 22. The anterior surfaces 15 and 17 form the anterior face 19 of the optic 12, while the posterior surfaces 20 and 22 form the posterior face 23 of the optic.

The central lens portion 16 is comprised of an optically clear material that is easily deformable when subjected to the action, that is the contraction or contractive force, exerted by the ciliary muscle of the eye. As noted above, the anterior and posterior lens portions 14 and 18 have a higher refractive index relative to the refractive index of the central lens portion 16 of optic 12.

The central lens portion 16 and the anterior and posterior lens portions 14 and 18 preferably are comprised of materials from the same basic chemical family. For example, the central lens portion 16 may be comprised of low or very low modulus silicone polymeric material having an index of refraction of at least about 1.37 or about 1.39, while the anterior and posterior lens portions 14 and 18 can be comprised of higher refractive index silicone, for example having an index of refraction of at least about 1.42 or at least about 1.44 or about 1.46 or about 1.48 or higher. The modulus of the silicone polymeric material making up the central lens portion 16 is, for example, no greater than about 20 psi.

Alternately, the central lens portion 16 can be comprised of a hydrophilic acrylic polymeric material, while the anterior and posterior lens portions 14 and 18 can be made of higher refractive index, rigid or deformable (for insertion) acrylic polymeric materials which can be either hydrophobic or hydrophilic.

One example of the materials used to produce the central lens portion 16 and the anterior and posterior lens portions 14 and 18 are as follows:

TABLE

POTENTIAL FORMULATIONS

| Component | Central | Anterior and Posterior Portions |
|---|---|---|
| 2-phenylpropyl acrylate | 50% wt. | 70% wt. |
| 2-phenylpropyl methacrylate | | |
| Ethylene glycol dimethacrylate | 0.5% wt. | 1.0% wt. |
| N-hexyl acrylate | 48.9% wt. | 28.4% wt. |
| UV chromophore (benzotriazole-type) | 0.5% wt. | 0.5% wt. |
| Initiator | 0.1% wt. | 0.1% wt. |

The present IOL 10 can be produced using conventional polymer processing techniques. For example, the present anterior and posterior lens portions 14 and 18 can be produced separately using conventional molding, for example, injection molding, techniques. These lens portions 14 and 16 can then be used to produce optic 12 using conventional molding techniques, for example, insert molding techniques, together with the material used to produce the central lens portion 16.

The optical powers of the lens portions 14, 16 and 18 may be controlled so as to satisfactorily address the needs of the patient in whose eye IOL 10 is inserted. Each of the lens portions 14, 16 and 18 can have a suitable optical power. Preferably, the anterior lens portion 14 has a higher optical power than the posterior lens portion 18. In one embodiment, the anterior lens portion 14 has a positive optical power, for example, a relatively high positive optical power such as about 20 to about 40 diopters above the baseline optical power, and the posterior lens portion 18 has a negative optical power, that is an optical power below the baseline optical power, for example, a relatively high negative optical power such as about 10 to about 20 diopters below the baseline optical power, with the baseline optical power being identified as the optical power for distance correction at infinity. For example, the anterior lens portion 14 can have a positive optical power, relative to the baseline, while the posterior lens portion 18 can have a negative optical power, relative to the baseline, with the central lens portion 16 having substantially no or plano optical power. The use of highly positive and highly negative optical powers extends the total accommodative dioptic change beyond that of the movement of a single lens design, because the same amount of movement is translated into a larger dioptic power change.

The optical power of the optic 12 is a combination of the optical powers of the individual lens portions 14, 16 and 18, and can be varied based on the individual optical powers of the portions 14, 16 and 18 and the degree of separation between the anterior lens portion 14 and the posterior lens portion 18.

The IOL 10 is sized to fit within the capsular bag of the eye so as to be reshapable in response to the action of the ciliary muscle 46 and zonules 48 on the capsular bag of the eye. The IOL 10 should be sized to facilitate the movement and reshaping of the optic 12 in response to the action of the ciliary muscle 46 and zonules 48. For example, if the optic 12 is too large, the ciliary muscle 46 and zonules 48 will be inhibited from effectively contracting/relaxing so that the amount of accommodating movement and reshaping will be unduly restricted. Of course, if the IOL 10 is too small, the optic 12 will be ineffective to focus light on the retina of the eye 40, may cause glare and/or may not cooperate with the eye to effect the desired amount of accommodating movement/reshaping. If the IOL 10 is to be included in an adult human eye, the optic 10 preferably has a diameter in the range of about 8 mm to amount 12 mm.

The IOL 10 can be inserted into the capsular bag 50 of the eye 40 using conventional equipment and techniques, for example, after the natural crystalline lens of the eye is removed, using a phacoemulsification technique.

The IOL 10 in the eye 40, as shown in FIGS. 2 and 3, is located so that the posterior face 20 of the central lens portion 16 and the posterior face 22 of the posterior lens portion 18 are in contact with the inner posterior wall 52 of the capsular bag 50. This contact is substantially maintained regardless of the configuration of the optic 12 in the eye 40. Such contact is effective in maintaining the structural integrity of the capsular bag 50 and, in addition, effectively inhibits the growth of cells from the capsular bag onto the optic, thereby at least inhibiting or reducing the severity of posterior capsular bag opacification (PCO).

Without wishing to limit the invention to any particular theory or mode of operation, the eye 40 is believed to act on optic 12 as follows. With the ciliary muscle being fully relaxed the tension of the zonules 48 causes the capsular bag to increase in diameter which causes optic 12 to become relatively thin. In this configuration, the separation between the anterior lens portion 14 and posterior lens portion 18 is at a minimum. Such configuration of optic 12 provides effective distance vision to the eye 40. This configuration is at least generally illustrated in FIG. 2. With IOL 10 in the position as shown in FIG. 2, far away or distant objects are brought into focus. If a near object is to be viewed, the ciliary muscle 46 contracts or constricts. The capsular bag 50 compresses, reshaping the optic 12 included therein, as shown in FIG. 3. This reshaping of the optic 12 causes the anterior lens portion 14 and posterior lens portion 18 to become relatively more separated. This reshaping of optic 12 provides near focus accommodation to allow the near object to be viewed.

The present IOL 10 has the ability, in cooperation with the eye, to be reshaped to provide for both distance focus and near focus.

One important advantage of the present IOL 10 is the presence of anterior lens portion 14 and posterior lens portion 18. Thus, not only does accommodation occur because of the reshaping of the central lens portion 16 and the axial movement of the anterior lens portion 14, but in addition, such reshaping causes the anterior and posterior lens portions 14 and 18 to separate further. This additional separation between the two lens portions 14 and 18 provides an additional degree of accommodation, particularly when the anterior lens portion is highly positive and the posterior lens portion in highly negative. Thus, the action of the ciliary muscle 46 and zonules 48 is amplified by the reshaping and the increased separation of optic 12.

IOL 10 is such that the amount of accommodation achievable preferably is in the range of about 1 to about 4 or about 5 or about 6 diopters.

Figure 4:
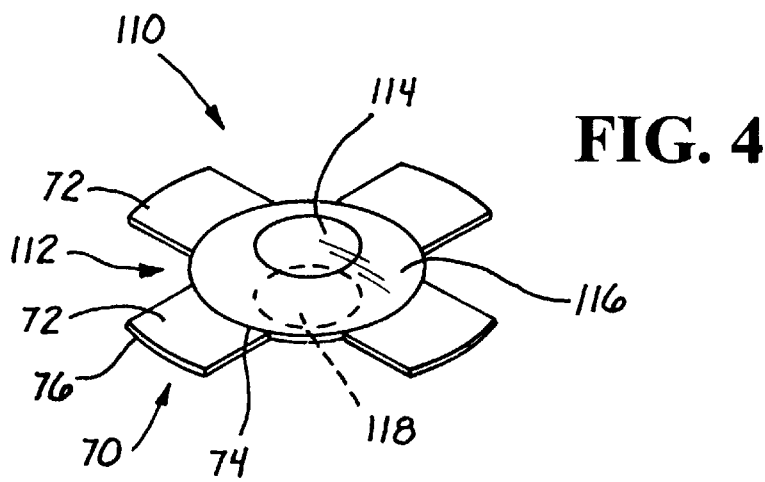
FIG. 4 is a top side view, in perspective, of an additional IOL in accordance with the present invention.
Figure 5:
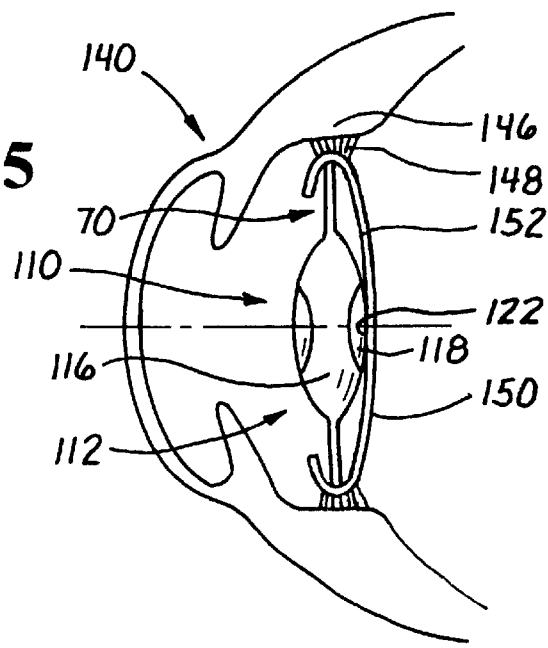
FIG. 5 is a fragmentary sectional view of an eye in which the IOL of FIG. 4 has been implanted with the lens being located in a resting position with the ciliary muscle of the eye in the relaxed state.
Figure 6:
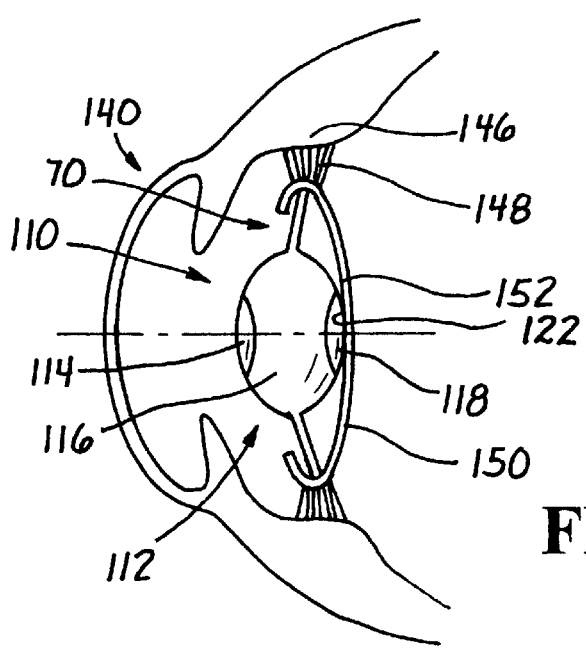
FIG. 6 is a fragmentary sectional view of an eye in which the IOL of FIG. 4 has been implanted, with the ciliary muscle of the eye in the contracted state.

FIGS. 4, 5 and 6 illustrate an additional IOL, shown generally at 110, in accordance with the present invention. Except as expressly described herein, additional IOL 110 is structured and functions similarly to IOL 10. Components of IOL 110 which correspond to components of IOL 10 are indicated by the same reference numerals increased by 100.

The primary difference between IOL 110 and IOL 10 relates to the presence in IOL 110 of a force transfer assembly, shown generally at 70. In particular, as best shown in FIG. 4, force transfer assembly 70 includes four identically structured transfer members 72 which extend radially outwardly from the proximal end 74, which is attached to optic 112, to an outer or distal end 76. Each of (the transfer members 72 has a substantially flat configuration and is made of an acrylic polymeric material which is deformable for insertion of the IOL 110 into the eye, yet is more rigid than the central lens portion 116 to facilitate the transfer of force from the eye 140 to the optic 112. One particularly useful acrylic polymeric material for use as a material of construction of the members 72 is a polymeric composition produced from the following mixture of monomers:

| | |
|---|---|
| Ethyl acrylate | 57.1% by weight |
| Ethyl methacrylate | 27.7% by weight |
| Trifluoroethyl methacrylate | 9.8% by weight |
| Ethylene glycol dimethacrylate | 3.8% by weight |
| UV chromophore | 1.5% by weight |
| Initiator (thermal) | 0.1% by weight |

The IOL 110 can be produced by injection molding the anterior lens portion 14, posterior lens portion 18 and transfer members 72 separately and then insert molding can be employed to form the combination of the anterior and posterior lens portions, the transfer members and the central lens portion 116.

With the force transfer assembly 70 in place, if the IOL 110 is to be included in an adult human eye, the optic 112 preferably has a diameter in the range of about 3.5 mm to about 7 mm, and the IOL 110 has an overall maximum diameter, including the force transfer assembly 70 in the rest state, that is fully extended from the optic 112, in the range of about 8 mm to about 12 mm.

Insertion can be accomplished using conventional techniques, for example, after the natural lens of the eye has been removed.

In the eye, IOL 110 moves axially in response to the action of the eye 140, which includes ciliary muscle 146 and zonules 148, through the force transfer assembly 70. In addition, the optic 112 is reshaped in response to the action of the eye 140 through force transfer assembly 70. The posterior surface 122 of posterior lens portion 118 remains in substantial contact with the inner posterior wall 152 of the capsular bag 150. Such contact occurs whether the IOL is located in its posterior most position in eye 140 or in its anterior most position in eye 140. Such contact inhibits the growth of cells from the capsular bag 150 onto optic 110 and inhibits PCO.

IOL 110 provides focus accommodation because of the reshaping of the optic 112, in much the same way as when optic 12 is reshaped. However, optic 112 provides further accommodation because of the axial movement of optic 112. Thus, optic 112 may provide additional or enhanced accommodation relative to optic 12.

The present invention provides accommodating IOLs which cooperate with the eye to achieve advantageous amounts, preferably enhanced amounts, of accommodation. Such accommodation, as described herein, is often increased, for example relative to previous accommodating IOLs.

While this invention has been described with respect to various specific examples and embodiments, it is to be understood that the invention is not limited thereto and that it can be variously practiced within the scope of the following claims.

What is claimed is:

1. An intraocular lens for use in a mammalian eye comprising:
an optic having a central optical axis and structured to focus light toward a retina of a mammalian eye and, in cooperation with the mammalian eye, to provide accommodation, the optic including
a first polymeric optic portion sized to move in response to an action of the mammalian eye; and
a second polymeric optic portion directly secured to the first optic portion at the central optical axis, positioned generally anterior of the first optic portion and having a higher index of refraction than the first optic portion, and being in continuous abutting relationship to the first optic portion at the central optical axis.

2. The intraocular lens of claim 1 wherein the first optic portion is sized to be reshaped in response to an action of the mammalian eye.

3. The intraocular lens of claim 1 wherein the first optic portion is sized to move axially in the mammalian eye in response to an action of the mammalian eye.

4. The intraocular lens of claim 1 wherein the optic includes an anterior face and the second optic portion includes an anterior surface which defines at least a portion of the anterior face of the optic.

5. The intraocular lens of claim 1 wherein the optic further comprises a third polymeric optic portion spaced apart from the second optic portion, secured to the first optic portion and having a higher index of refraction than the first optic portion.

6. The intraocular lens of claim 5 wherein the second optic portion is positioned anterior of the third optic portion and the second optic portion has a higher optical power than the third optic portion.

7. The intraocular lens of claim 6 wherein the third optic portion has a negative optical power.

8. The intraocular lens of claim 1 which further comprises a force transfer assembly having a first end coupled to the optic and a second end extending away from the optic and adapted to contact a posterior bag of the mammalian eye when the intraocular lens is located in the mammalian eye, the force transfer assembly being adapted to transfer a force exerted by the eye to the optic to facilitate movement of the optic.

9. The intraocular lens of claim 8 wherein the force transfer assembly is adapted to transfer a force exerted by the eye to the optic to facilitate at least one of reshaping the first optic portion in response to an action of the mammalian eye and moving the first optic portion axially in the mammalian eye in response to an action of the mammalian eye.

10. The intraocular lens of claim 1 wherein the second optic portion is substantially rigid in response to forces exerted on the second optic portion by the eye.

11. The intraocular lens of claim 1 wherein the first optic portion and the second optic portion are made of compatible materials.

12. The intraocular lens of claim 1 wherein the first optic portion and the second optic portion are made of different polymeric materials of the same general chemical family.

13. The intraocular lens of claim 1 wherein the intraocular lens is sized and structured to come into contact with a peripheral wall of a capsular bag of the mammalian eye when the intraocular lens is in use in the mammalian eye.

14. An intraocular lens for use in a mammalian eye comprising:
an optic having a central optical axis and structured to focus light toward a retina of a mammalian eye and, in cooperation with the mammalian eye, to provide accommodation, the intraocular lens being sized and structured to come into contact with a peripheral wall of a capsular bag of the mammalian eye when the intraocular lens is in use in the mammalian eye, the optic including
a first polymeric optic portion sized to move in response to an action of the mammalian eye; and
a second polymeric optic portion directly secured to the first optic portion at the central optical axis, positioned generally anterior of the first optic portion and in continuous abutting relationship to the first optic portion at the central optical axis, the first and second optic portions comprising different materials, respectively.

15. The intraocular lens of claim 14 wherein the first optic portion is sized to be reshaped in response to an action of the mammalian eye.

16. The intraocular lens of claim 14 wherein the first optic portion is sized to move axially in the mammalian eye in response to an action of the mammalian eye.

17. The intraocular lens of claim 14 wherein the optic includes an anterior face and the second optic portion includes an anterior surface which defines at least a portion of the anterior face of the optic.

18. The intraocular lens of claim 14 which further comprises a force transfer assembly having a first end coupled to the optic and a second end extending away from the optic and adapted to contact the capsular bag of the mammalian eye when the intraocular lens is in use in the mammalian eye, the force transfer assembly being adapted to transfer a force exerted by the eye to the optic to facilitate movement of the optic.

19. The intraocular lens of claim 14 wherein the optic is deformable for insertion into the mammalian eye through a small incision, and the first optic portion is more deformable than the second optic portion.

20. The intraocular lens of claim 14 wherein the second optic portion is substantially rigid in response to forces exerted on the second optic portion by the eye.

21. An intraocular lens for use in a mammalian eye comprising:
an optic having a central optical axis, structured to focus light toward a retina of a mammalian eye and, in cooperation with the mammalian eye, to provide accommodation, the optic including
a first polymeric optic portion sized to move in response to an action of the mammalian eye;
a second polymeric optic portion directly secured to the first optic portion at the central optical axis and positioned generally anterior of the first optic portion; and
a third polymeric optic portion directly secured to the first optic portion at the central optical axis and positioned generally posterior of the first optic portion, the first and second optic portions comprising different materials, respectively.

22. The intraocular lens of claim 21 wherein the first optic portion is sized to be reshaped in response to an action of the mammalian eye.

23. The intraocular lens of claim 21 wherein the first optic portion is sized to move axially in the mammalian eye in response to an action of the mammalian eye.

24. The intraocular lens of claim 23 wherein the first optic portion is further sized to be reshaped in response to an action of the mammalian eye.

25. The intraocular lens of claim 21 wherein the optic includes an anterior face and a posterior face, and the second optic portion includes an anterior surface which defines at least a portion of the anterior face of the optic and the third optic portion includes a posterior surface which defines at least a portion of the posterior face of the optic.

26. The intraocular lens of claim 21 wherein the second optic portion has a higher optical power than the third optic portion.

27. The intraocular lens of claim 26 wherein the third optic portion has a negative optical power, and the first and third optic portions comprise different materials, respectively.

28. The intraocular lens of claim 21 which further comprises a force transfer assembly having a first end coupled to the optic and a second end extending away from the optic and adapted to contact a capsular bag of the mammalian eye when the intraocular lens is in use in the mammalian eye, the force transfer assembly being adapted to transfer a force exerted by the eye to the optic to facilitate movement of the optic.

29. The intraocular lens of claim 21 wherein the second optic portion and the third optic portion are substantially rigid in response to forces exerted on the second optic portion and the third optic portion, respectively, by the eye.

30. The intraocular lens of claim 21 wherein the first optic portion and the second optic portion and the third optic portion are made of compatible materials, the optic has a central optical axis and at least one of the second and third optic portions is in continuous abutting relationship to the first optic portion along the central optical axis.

31. The intraocular lens of claim 21 wherein the intraocular lens is sized and structured to come into contact with a peripheral wall of a capsular bag of the mammalian eye when the intraocular lens is in use in the mammalian eye.

* * * * *